US012685855B2

(12) United States Patent
Ryan

(10) Patent No.: US 12,685,855 B2
(45) Date of Patent: Jul. 21, 2026

(54) MEDICAL DEVICE WITH ANTI-PEELING FLASH FEATURE

(71) Applicant: Becton, Dickinson and Company, Franklin Lakes, NJ (US)

(72) Inventor: Kevin M. Ryan, Whitehouse Station, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 779 days.

(21) Appl. No.: 17/990,056

(22) Filed: Nov. 18, 2022

(65) Prior Publication Data

US 2024/0165389 A1     May 23, 2024

(51) Int. Cl.
*A61M 39/16*     (2006.01)
*A61M 39/20*     (2006.01)

(52) U.S. Cl.
CPC .......... *A61M 39/162* (2013.01); *A61M 39/20* (2013.01); *A61M 2209/06* (2013.01)

(58) Field of Classification Search
CPC . A61M 39/162; A61M 39/20; A61M 2209/06
See application file for complete search history.

(56) References Cited

U.S. PATENT DOCUMENTS

| | | | |
|---|---|---|---|
| 8,671,496 B2 | 3/2014 | Vaillancourt et al. | |
| 8,696,820 B2 | 4/2014 | Vaillancourt et al. | |
| 8,740,864 B2 | 6/2014 | Hoang et al. | |

| | | | |
|---|---|---|---|
| 9,039,989 B2 | 5/2015 | Liu et al. | |
| 9,283,369 B2 | 3/2016 | Ma et al. | |
| 9,399,125 B2 | 7/2016 | Burkholz | |
| 9,480,833 B2 | 11/2016 | Hoang et al. | |
| D834,187 S | 11/2018 | Ryan | |
| 10,376,686 B2 | 8/2019 | Burkholz et al. | |
| 10,413,716 B2 | 9/2019 | Sathe | |
| 11,083,883 B2 | 8/2021 | Ryan et al. | |
| 11,273,298 B2 | 3/2022 | Erekovcanski et al. | |
| 11,344,715 B2 | 5/2022 | Erekovcanski et al. | |
| 11,353,147 B2 | 6/2022 | Marici et al. | |
| 11,389,636 B2 | 7/2022 | Coyle | |
| 2008/0086091 A1* | 4/2008 | Anderson | A61M 39/162 604/263 |
| 2010/0000040 A1* | 1/2010 | Shaw | A61M 39/16 15/244.1 |
| 2012/0302968 A1 | 11/2012 | Tennican | |
| 2012/0302997 A1 | 11/2012 | Gardner et al. | |
| 2013/0035667 A1 | 2/2013 | Anderson et al. | |
| 2013/0178804 A1 | 7/2013 | Tennican | |
| 2013/0197485 A1 | 8/2013 | Gardner et al. | |
| 2014/0135739 A1 | 5/2014 | Solomon et al. | |
| 2015/0005699 A1 | 1/2015 | Burbank et al. | |
| 2015/0086441 A1 | 3/2015 | She et al. | |
| 2016/0106968 A1 | 4/2016 | Solomon et al. | |

(Continued)

FOREIGN PATENT DOCUMENTS

WO     2016163712 A1     10/2016

*Primary Examiner* — Bradley J Osinski
(74) *Attorney, Agent, or Firm* — Servilla Whitney LLC

(57)     ABSTRACT

A medical device includes a body having a first end and a second end positioned opposite the first end, with the body defining an opening extending from the first end and including a sealing surface extending radially outward from the opening. At least a portion of the sealing surface includes a non-circular perimeter pattern.

13 Claims, 7 Drawing Sheets

(56)     References Cited

U.S. PATENT DOCUMENTS

| | | |
|---|---|---|
| 2016/0144118 A1 | 5/2016 | Solomon et al. |
| 2016/0310720 A1 | 10/2016 | Solomon et al. |
| 2018/0055962 A1 | 3/2018 | Drmanovic |
| 2018/0064604 A1 | 3/2018 | Drmanovic |
| 2018/0071508 A1 | 3/2018 | Drmanovic |
| 2018/0085568 A1 | 3/2018 | Drmanovic |
| 2018/0200500 A1 | 7/2018 | Ziebol et al. |
| 2018/0214242 A1 | 8/2018 | Davis et al. |
| 2018/0214684 A1 | 8/2018 | Avula et al. |
| 2018/0250194 A1 | 9/2018 | Drmanovic |
| 2018/0256804 A1 | 9/2018 | Burbank et al. |
| 2018/0256880 A1 | 9/2018 | Follman et al. |
| 2018/0256881 A1 | 9/2018 | Hitchcock et al. |
| 2018/0256883 A1 | 9/2018 | Follman et al. |
| 2018/0369562 A1 | 12/2018 | Gardner et al. |
| 2019/0038888 A1 | 2/2019 | Gardner |
| 2019/0099593 A1 | 4/2019 | Avula et al. |
| 2019/0117332 A1 | 4/2019 | Davis et al. |
| 2019/0201681 A1 | 7/2019 | Ziebol et al. |
| 2019/0234540 A1* | 8/2019 | Marici ................ A61M 39/165 |
| 2019/0262525 A1 | 8/2019 | Wyeth et al. |
| 2019/0282795 A1 | 9/2019 | Fangrow |
| 2019/0351212 A1 | 11/2019 | Dudar et al. |
| 2020/0121858 A1 | 4/2020 | Anderson et al. |
| 2020/0139037 A1 | 5/2020 | Ziebol et al. |
| 2020/0155794 A1 | 5/2020 | Ziebol |
| 2020/0197686 A1 | 6/2020 | Anderson et al. |
| 2020/0238070 A1 | 7/2020 | Ryan |
| 2021/0001110 A1* | 1/2021 | Bedoe ................... A61M 39/20 |
| 2021/0093791 A1 | 4/2021 | Anderson et al. |
| 2021/0275707 A1 | 9/2021 | Jiang et al. |
| 2021/0322749 A1 | 10/2021 | Rothenberg et al. |
| 2021/0322750 A1 | 10/2021 | Harandi et al. |
| 2021/0322751 A1 | 10/2021 | Jiang et al. |
| 2021/0322752 A1 | 10/2021 | Jiang et al. |
| 2022/0023609 A1 | 1/2022 | Coyle |

* cited by examiner

MEDICAL DEVICE WITH ANTI-PEELING FLASH FEATURE

BACKGROUND OF THE INVENTION

Field of the Invention

The present disclosure relates to a medical device with an anti-peeling flash feature for use with a packing film

Description of Related Art

Male and female disinfecting cap devices are commonly utilized for disinfecting various medical devices, such as luer connectors or catheter connectors. These disinfecting caps are typically made of an injection moldable thermoplastic, of cylindrical design, with at-least one open end.

Referring to FIG. 1, a disinfecting cap 1 has a sealing surface 2 feature formed by a flat circular area tangent to an open end 3 of the cap 1, such that it can be thermally (heat) sealed closed at manufacturing with a web peel film packaging. The peel film packaging keeps the disinfecting solution or contents of the disinfecting cap 1 from evaporating during shipping and storage. When the cap 1 is ready for use by a clinician, the peel film packaging is peeled away from the cap 1 opening such that the disinfecting cap 1 can be placed on a medical device.

A disadvantage of the disinfecting caps use of a flat circular sealing surface is that the cap's sealing surface is prone to deformation during the heat sealing process of sealing the peel film web packaging. In particular, the deformation may take the form of flash (similar to flash that may occur during injection molding), where the cap sealing surface material deforms or extrudes out into a thin film that expands out and radially away from the sealing surface. This flash film typically occurs radially outward away from the cap opening, but may form inward, towards the center of the cap opening. When a clinician opens the cap by peeling the peel film web away from the cap, this flash can partially stick to the peel film and tear away from the cap sealing surface, forming a plastic string or debris. The length of these plastic strings have been observed to be up to half of the circumference of an outer sealing surface perimeter of the cap. Such plastic strings can be a medical issue if they become detached and ingress into a fluid path, such as a catheter fluid path via a catheter hub or connector.

SUMMARY OF THE INVENTION

In one aspect or embodiment, a medical device includes a body having a first end and a second end positioned opposite the first end, with the body defining an opening extending from the first end and including a sealing surface extending radially outward from the opening. At least a portion of the sealing surface includes a non-circular perimeter pattern.

An entirety of the sealing surface may include the non-circular perimeter pattern. The non-circular perimeter pattern may be co-planar with the sealing surface. The non-circular perimeter pattern may be a sawtooth shape. The non-circular perimeter pattern may be a plurality of triangles, with a plurality of triangle-shaped recessed areas defined between the non-circular perimeter pattern and an outer edge of the first end of the body. At least a portion of the non-circular perimeter pattern may extend to an outer edge of the first end of the body. The medical device may be a disinfecting cap, where the second end of the body is closed. An inner surface of the opening of the body may be threaded. The first end may include a flange extending radially outward from the body, where at least a portion of the sealing surface is provided on the flange. The body may include a plurality of ribs extending in a direction from the first end of the body toward the second end of the body. The medical device may further include a packaging film thermally adhered to the sealing surface. The packaging film may form a fluid tight seal with the body.

In a further aspect or embodiment, a medical device includes a body having a first end and a second end positioned opposite the first end, with the body defining an opening extending from the first end and including a sealing surface extending radially outward from the opening. At least a portion of the sealing surface may include a plurality of recessed areas.

Each of the plurality of recessed areas may be rectangular. Each of the plurality of recessed areas may be sloped. Each of the plurality of recessed areas may be spaced from each other.

DESCRIPTION OF THE INVENTION

Figure 1:
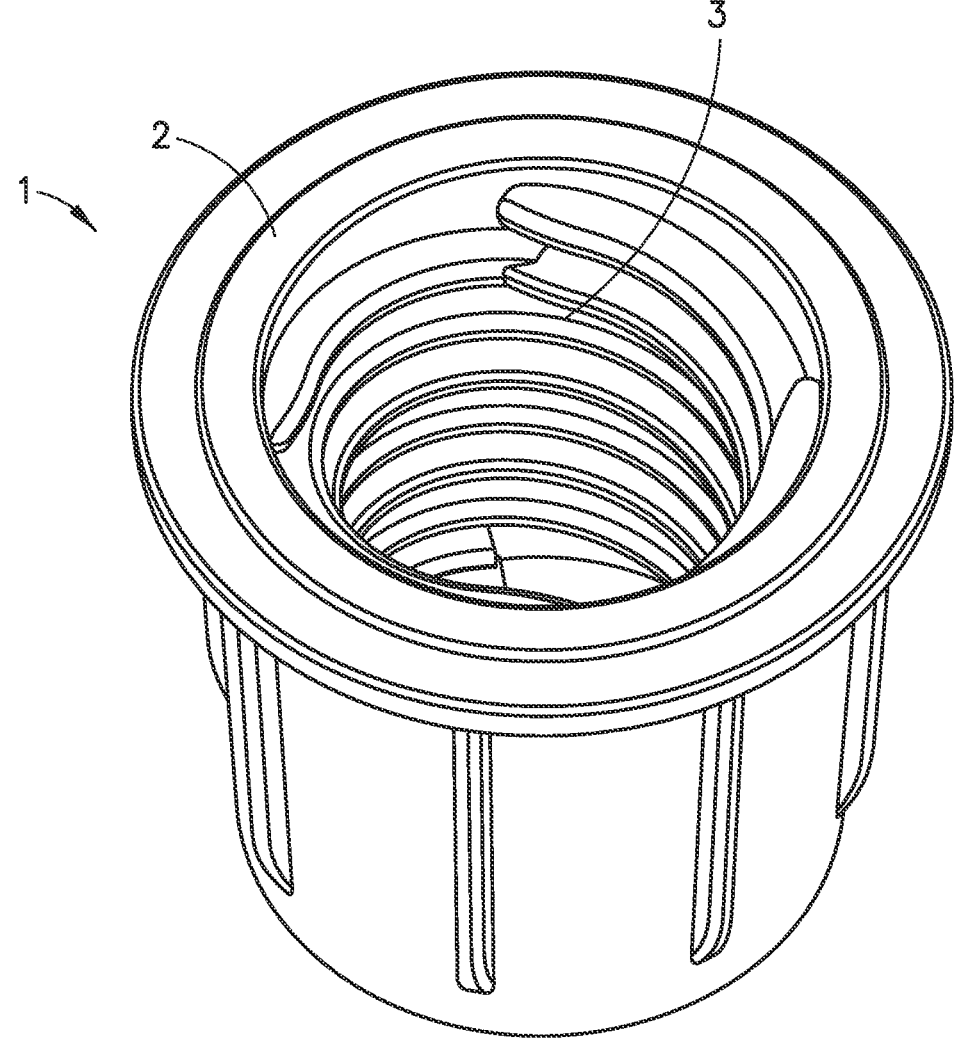
FIG. 1 is a perspective view of a prior art disinfecting cap.
Figure 2:
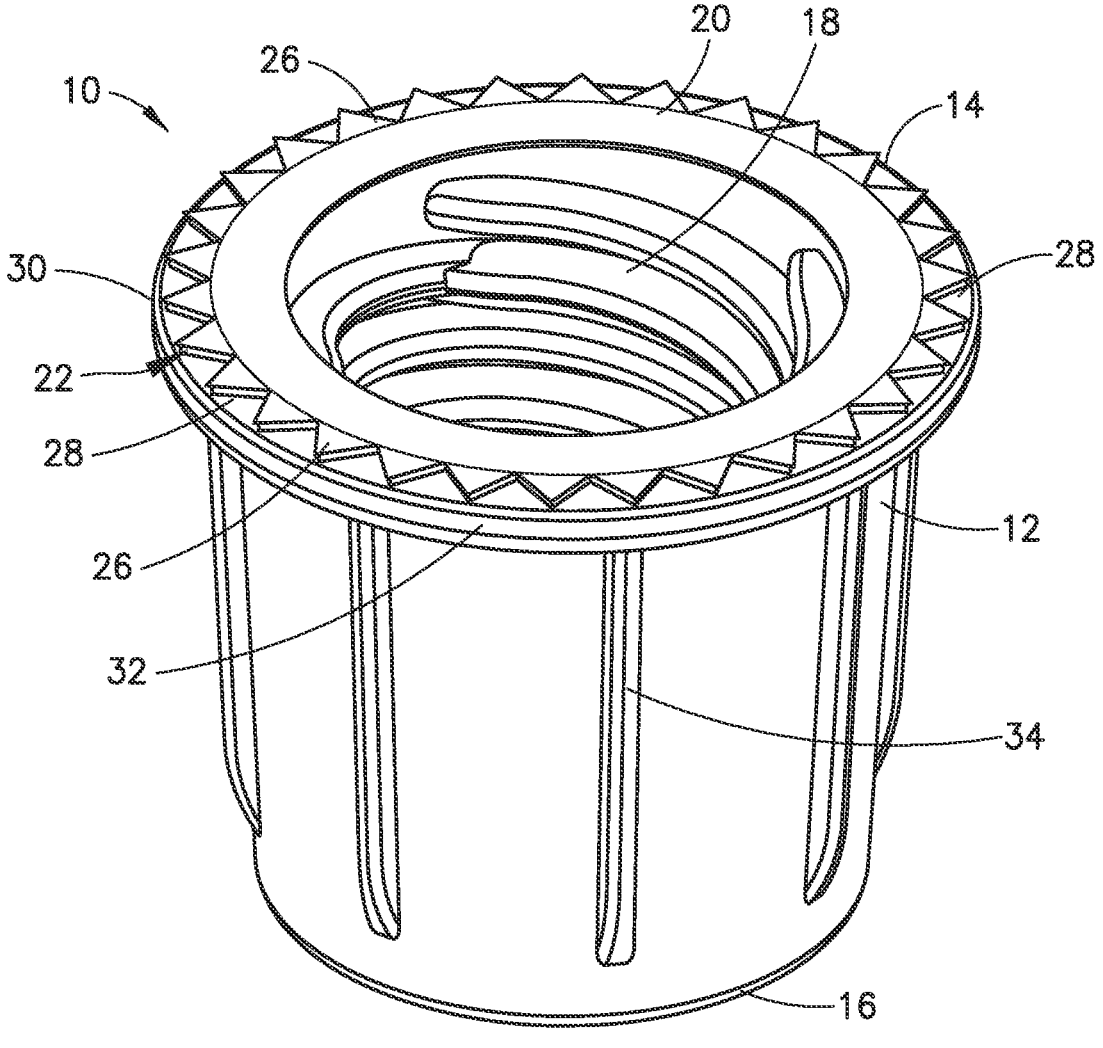
FIG. 2 is a perspective view of a medical device according to one aspect or embodiment of the present application.

The following description is provided to enable those skilled in the art to make and use the described embodiments contemplated for carrying out the invention. Various modifications, equivalents, variations, and alternatives, however, will remain readily apparent to those skilled in the art. Any and all such modifications, equivalents, variations, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 2-6, a medical device 10 according to one aspect or embodiment of the present application, includes a body 12 having a first end 14 and a second end 16 positioned opposite the first end 14, with the body 12 defining an opening 18 extending from the first end 14 and including a sealing surface 20 extending radially outward from the opening 18. At least a portion of the sealing 20 includes a non-circular perimeter pattern 22. The non-circular perimeter pattern 22 is configured to prevent the formation of plastic strings or debris during separation of a packaging film 24 from the sealing surface 20 of the medical device 10. The non-circular perimeter pattern 22 is configured to provide a plurality of stress concentration points to ensure any flashing created when the packaging film 24 is thermally sealed to the sealing surface 20 separates from the packaging film 24 when the packaging film 24 is peeled or removed from the sealing surface 20. Accordingly, rather than forming plastic strings, the non-circular perimeter pattern 22 is configured to ensure separation of any flashing from the packaging film 24 such that any flashing remains connected to the body 12 of the medical device 10.

Figure 3:
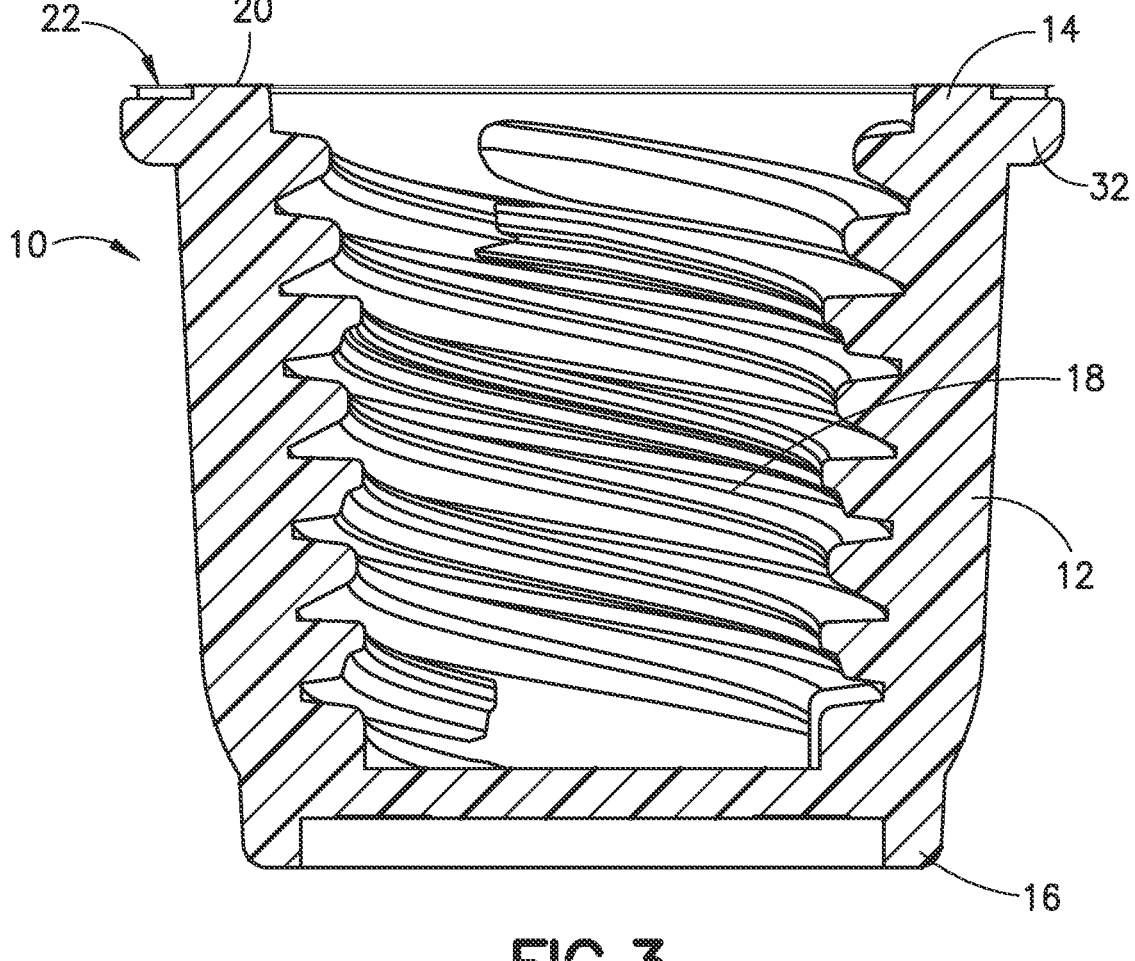
FIG. 3 is a cross-sectional view of the medical device of FIG. 2.
Figure 4:
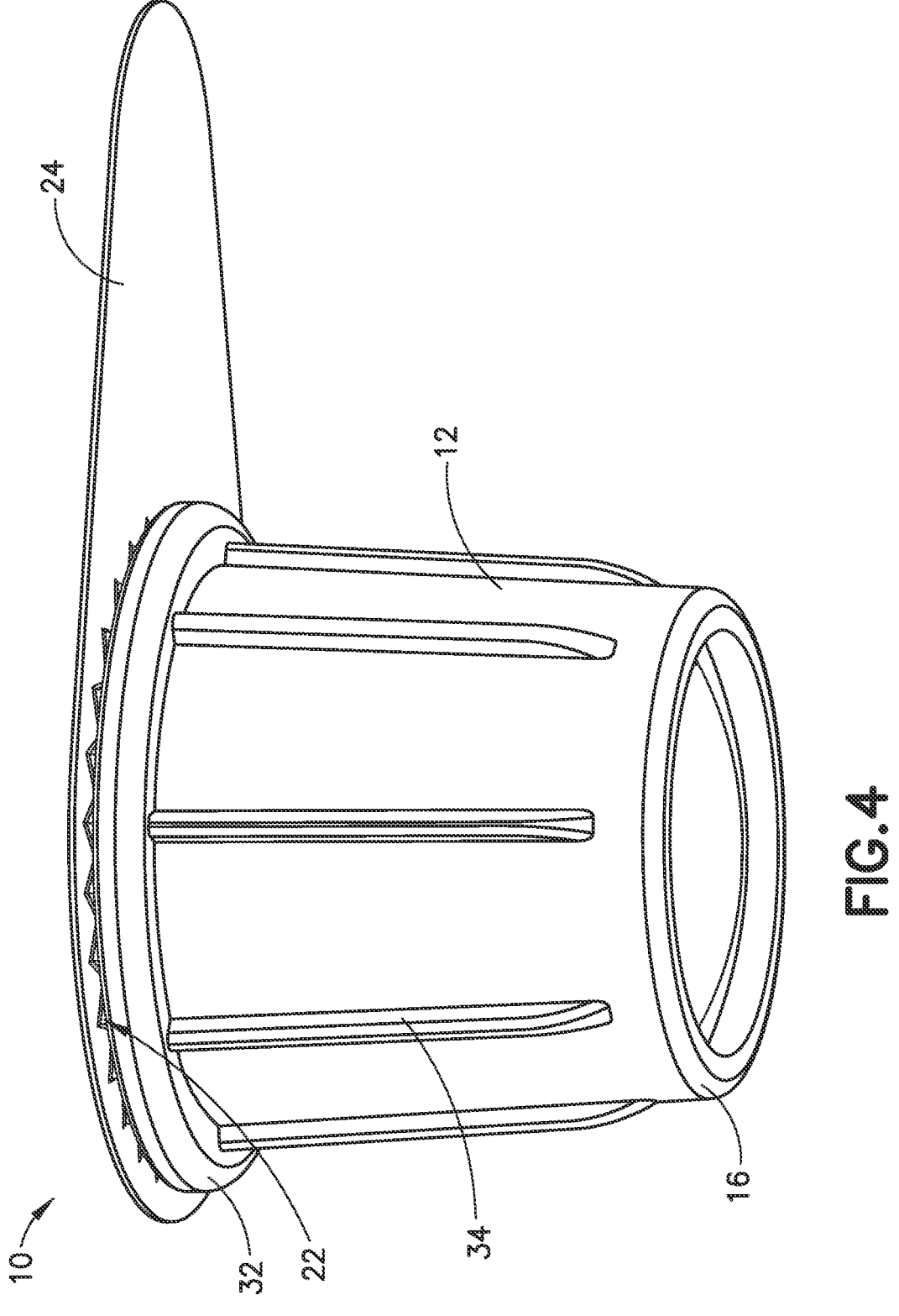
FIG. 4 is a perspective view of the medical device of FIG. 2, showing the medical device with a packaging film.
Figure 5:
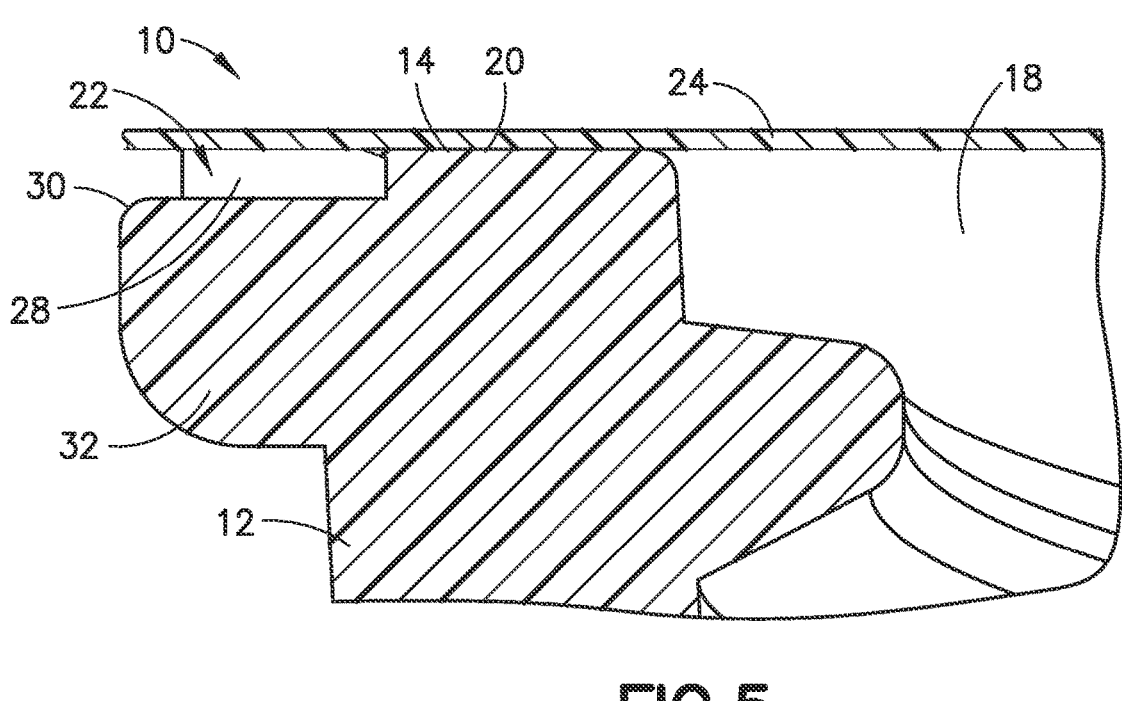
FIG. 5 is partial cross-sectional view of the medical device of FIG. 2, showing the medical device with a packaging film and no flash defect.
Figure 6:
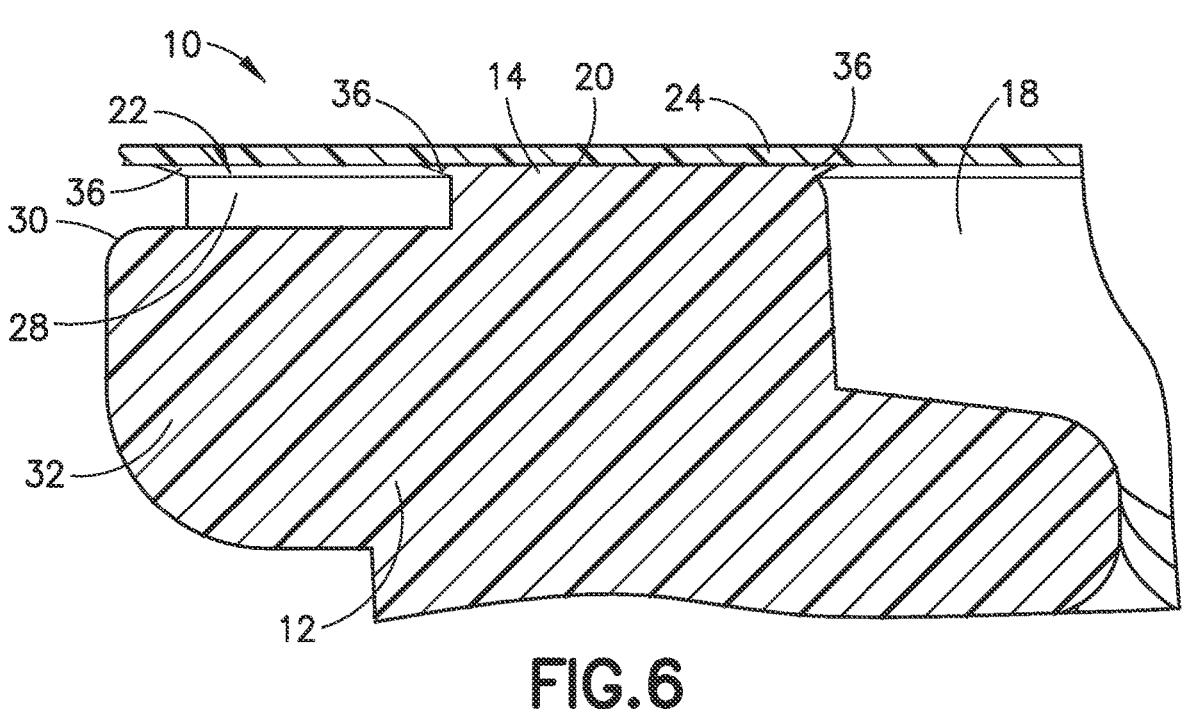
FIG. 6 is partial cross-sectional view of the medical device of FIG. 2, showing the medical device with a packaging film and flash defect.

Referring again to FIGS. 2-6, in one aspect or embodiment, the medical device 10 is a disinfecting cap, such as a cap for disinfecting another medical device, medical connector, catheter connector, etc. In some aspects or embodiments, the medical device 10 is a medical connector. As shown in FIG. 3, the second end 16 of the body 12 is closed. An inner surface of the opening 18 of the body is threaded to allow the body 12 to be threaded onto a mating connector, although other suitable arrangements may be utilized. The first end 14 includes a flange 32 extending radially outward from the body 12, with at least a portion of the sealing surface 20 provided on the flange 32. The body 12 includes a plurality of ribs 34 extending in a direction from the first end 14 of the body 12 toward the second end 16 of the body 12. The plurality of ribs 34 are configured to provide a gripping surface to enable a clinician to more easily grasp and turn the medical device 10. As shown in FIGS. 4-6, in some aspects or embodiments, the medical device 10 includes the packaging film 24 thermally adhered to the sealing surface 20. The packaging film 24 forms a fluid tight seal with the body 12. The body 12 may contain a disinfecting fluid within the opening 18, with the packaging film 24 preventing evaporation or spillage of the fluid from the opening 18.

Referring to FIG. 6, when the packaging film 24 is thermally adhered to the sealing surface 20 of the body 12, flashing or melting 36 of the body 12 may occur at several points on the first end 14 of the body 12. The stress concentration points formed by the non-circular perimeter pattern 22 are configured to enable separation of the packaging film 24 from the flashing or flash 36 when the packaging film 24 is removed from the body 12 during use of the medical device 10.

Referring to FIG. 6, when the packaging film 24 is thermally adhered to the sealing surface 20 of the body 12, flashing or melting 36 of the body 12 may occur at several points on the first end 14 of the body 12. The stress concentration points formed by the non-circular perimeter pattern 22 are configured enable separation of the packaging film 24 from the flashing or flash 36 when the packaging film 24 is removed from the body 12 during use of the medical device 10.

Figure 7:
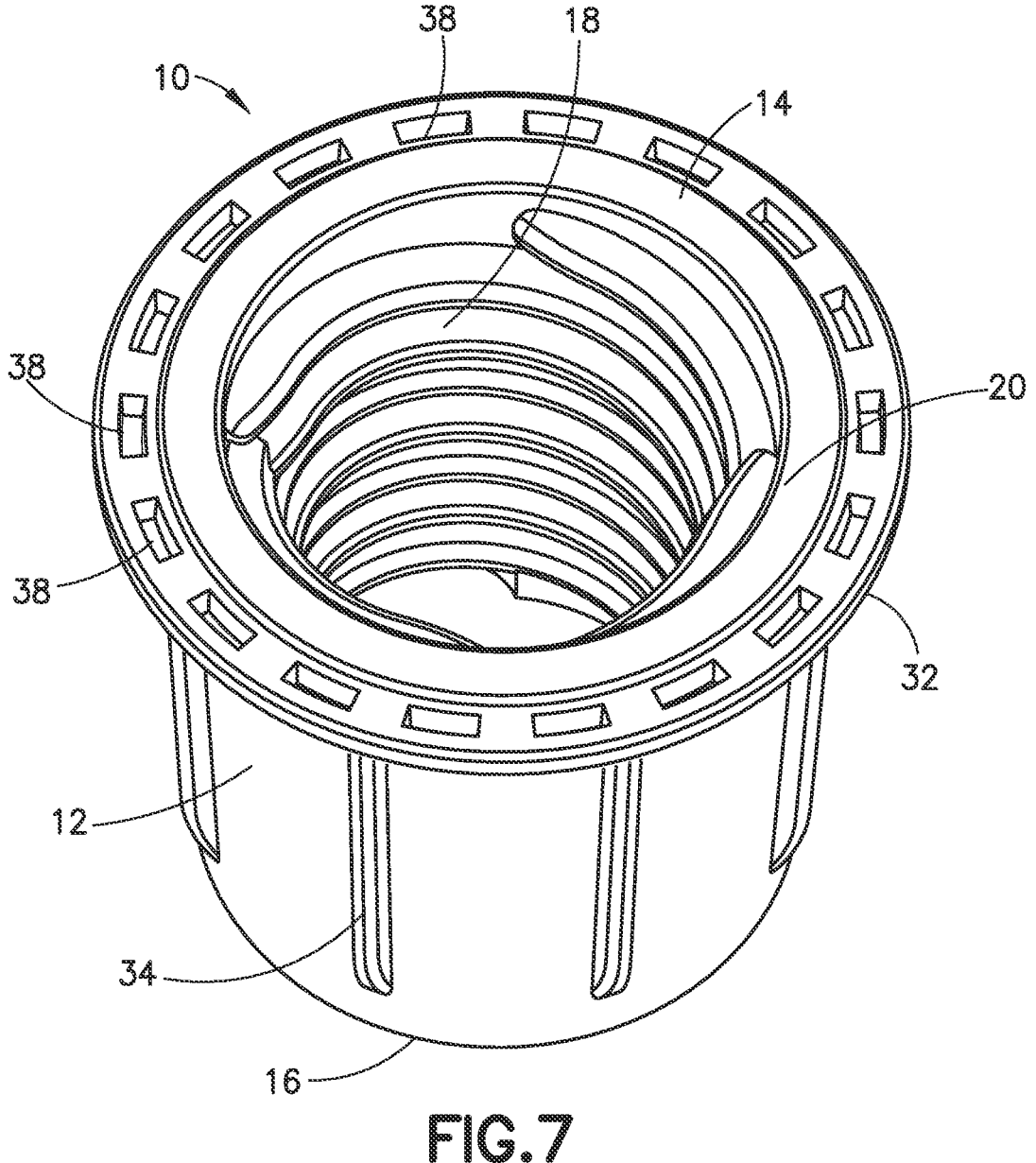
FIG. 7 is perspective view of a medical device according to a further aspect or embodiment of the present application.

Referring to FIG. 7, in a further aspect or embodiment, at least a portion of the sealing surface 20 includes a plurality of recessed areas 38 rather than the non-circular perimeter pattern 22. The plurality of recessed areas 38 may function similarly to the non-circular perimeter pattern 22 described above. Each of the plurality of recessed areas 38 are rectangular, although other suitable shapes may be utilized. Each of the plurality of recessed areas 38 are sloped, although the recessed areas 38 may be flat-bottomed in some aspects or embodiments. Each of the plurality of recessed areas 38 are spaced from each other. The plurality of recessed areas 38 are formed around the perimeter of the sealing surface 20 and are positioned at the outer edge 30 of the first end 14 of the body 12, although other suitable arrangements may be utilized.

Figure 8:
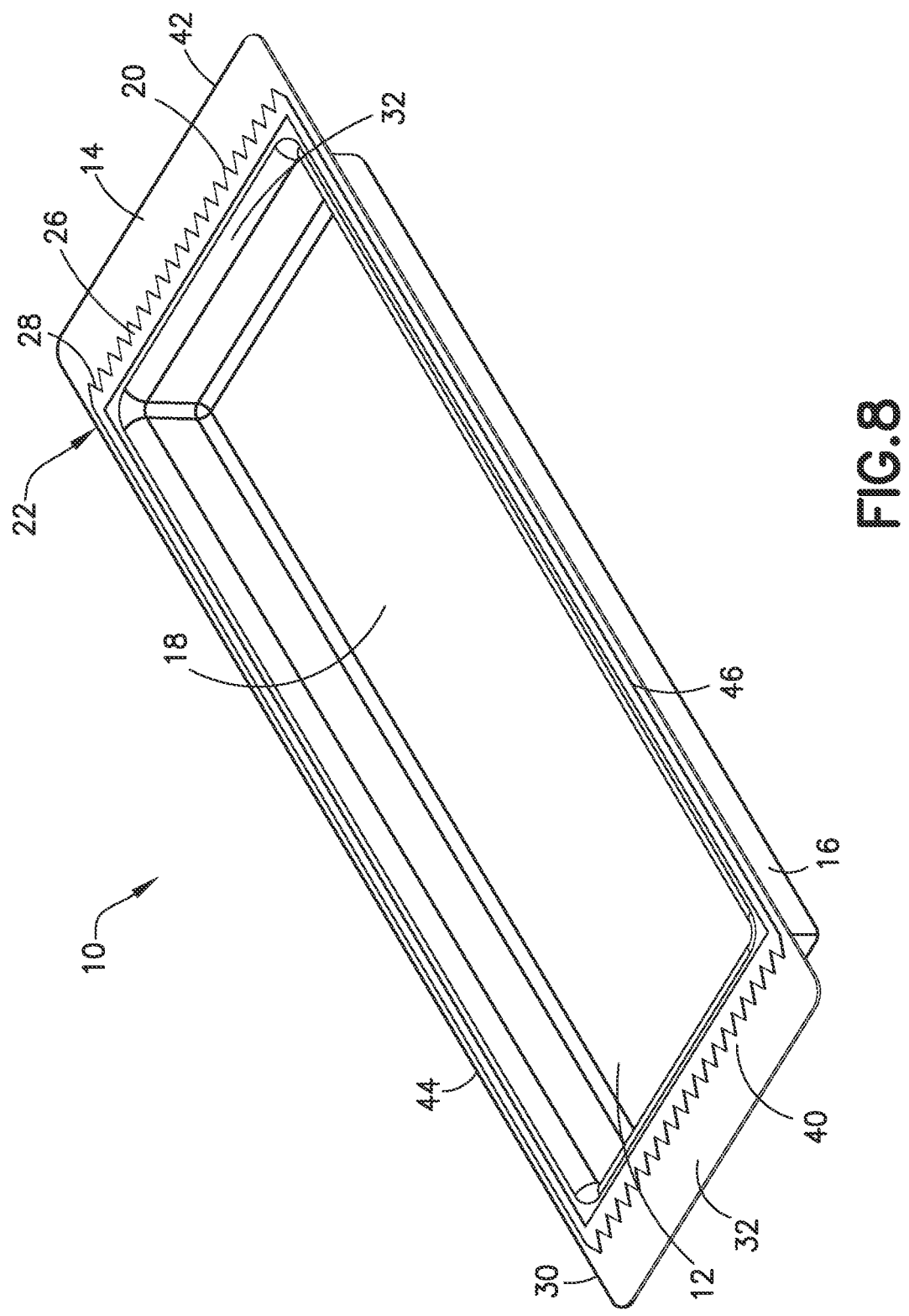
FIG. 8 is a perspective view of a medical device according to a further aspect or embodiment of the present application.

Referring to FIG. 8, in a further aspect or embodiment, the medical device 10 is packaging or a tray, with the sealing surface 20 with the packaging film 24 configured to be thermally sealed to the sealing surface 20 in the same manner as discussed above. Rather than being circular, the medical device 10 may be square or rectangular in shape and include a first side 40, a second side 42 positioned opposite the first side 40, a third side 44, and a fourth side 46 positioned opposite the third side. The sealing surface 20 also includes the non-circular perimeter pattern 22. As shown in FIG. 8, in some aspects or embodiments, the non-circular perimeter pattern 22 only includes the triangles 26 and recessed areas 28 at the first side 40 and the second side 42, with straight or linear portion of the sealing surface extending along the third side 44 and the fourth side. The non-circular perimeter pattern 22 is aligned parallel with a peel line of the packaging film 24. The non-circular perimeter pattern 22 may not be along an intended direction of peel, which is normal to the peel line.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A medical device comprising:
a body having a first end including a flange extending radially outwardly from the body to an outer edge and a second end positioned opposite the first end, the body defining an opening extending from the first end and including a sealing surface extending radially outward from the opening, and the body including a plurality of ribs extending radially outwardly from the body in a direction from the flange to the second end;
at least a portion of the sealing surface on the flange including a non-circular perimeter pattern co-planar with the sealing surface, extending to the outer edge and a plurality of recessed areas on the flange defined between the non-circular perimeter pattern and the outer edge; and
a packaging film thermally sealed to the sealing surface that extends radially outward from the opening and the non-circular perimeter pattern configured to ensure flash defects created during thermal sealing of the packaging film remain connected to the body of medical device and provide a plurality of stress concentration points to prevent formation of plastic strings or debris during separation of the packaging film from the sealing surface caused by the flash defects.

2. The medical device of claim 1, wherein an entirety of the sealing surface includes the non-circular perimeter pattern.

3. The medical device of claim 1, wherein the body contains disinfecting fluid in the opening.

4. The medical device of claim 1, wherein the non-circular perimeter pattern comprises a sawtooth shape.

5. The medical device of claim 1, wherein the non-circular perimeter pattern comprises a plurality of triangles, with a plurality of triangle-shaped recessed areas defined between the non-circular perimeter pattern and an outer edge of the first end of the body.

6. The medical device of claim 1, wherein at least a portion of the plurality of stress concentration points are positioned at the outer edge of the first end of the body.

7. The medical device of claim 1, wherein the medical device comprises a disinfecting cap, and wherein the second end of the body is closed.

8. The medical device of claim 7, wherein an inner surface of the opening of the body is threaded.

9. The medical device of claim 1, wherein the packaging film forms a fluid tight seal with the body.

10. A medical device comprising:

a body having a first end including a flange extending radially outwardly from the body to an outer edge and a second end positioned opposite the first end, the body defining an opening extending from the first end and including a sealing surface extending radially outward from the opening;

at least a portion of the sealing surface on the flange including a plurality of recessed areas formed around a perimeter of the sealing surface that extends radially outward from the opening and positioned at the outer edge of the first end; and a packaging film thermally sealed to the plurality of recessed areas and the sealing surface that extends radially outward from the opening, the plurality of recessed areas configured to ensure flash defects created during thermal sealing of the packaging film remain connected to the body of medical device and provide a plurality of stress concentration points to prevent formation of plastic strings or debris during separation of the packaging film from the sealing surface caused by the flash defects.

11. The medical device of claim 10, wherein each recessed area of the plurality of recessed areas is rectangular.

12. The medical device of claim 11, wherein each recessed area of the plurality of recessed areas is sloped.

13. The medical device of claim 11, wherein the plurality of recessed areas is a plurality of evenly spaced recessed areas.

* * * * *